United States Patent
Ho

(10) Patent No.: US 8,657,800 B2
(45) Date of Patent: Feb. 25, 2014

(54) SUCTION DEVICE HAVING A ROTARY SWITCH

(75) Inventor: Hsuan-Chiao Ho, Tongluo Township, Misoli County (TW)

(73) Assignee: Pacific Hospital Supply Co., Ltd., Miaoli County (TW)

(*) Notice: Subject to any disclaimer, the term of this patent is extended or adjusted under 35 U.S.C. 154(b) by 0 days.

(21) Appl. No.: 13/480,220

(22) Filed: May 24, 2012

(65) Prior Publication Data
US 2013/0312755 A1 Nov. 28, 2013

(51) Int. Cl.
*A61M 1/00* (2006.01)
*A62B 19/00* (2006.01)
*A62B 18/08* (2006.01)

(52) U.S. Cl.
USPC ........... 604/319; 604/320; 604/323; 604/326; 604/283; 128/205.12; 128/207

(58) Field of Classification Search
USPC .................. 604/320, 323, 326, 319, 283; 128/205.12, 207, 14
See application file for complete search history.

(56) References Cited

U.S. PATENT DOCUMENTS

| | | | | |
|---|---|---|---|---|
| 5,775,325 A * | 7/1998 | Russo | ...................... | 128/205.12 |
| 5,919,174 A * | 7/1999 | Hanson | ......................... | 604/533 |
| 6,415,789 B1 * | 7/2002 | Freitas et al. | ............ | 128/202.27 |
| 6,543,451 B1 * | 4/2003 | Crump et al. | ............ | 128/207.14 |
| 2010/0147310 A1 * | 6/2010 | Brewer et al. | ............ | 128/207.14 |

* cited by examiner

*Primary Examiner* — Tatyana Zalukaeva
*Assistant Examiner* — Andrew J Mensh
(74) *Attorney, Agent, or Firm* — Chun-Ming Shih; HDLS IPR Services

(57) ABSTRACT

A suction device having a rotary switch is provided. A main body of the suction device is provided with a patient-end connector, an oxygen supply connector, a suction connector, a cleaning connector and a connecting portion. The rotary switch is assembled with the connecting portion and can be switched between a first position and a second position. The rotary switch is provided with two opposite suction holes. When the rotary switch is located in the first position, the two suction holes are aligned with the patient-end connector and the suction connector to thereby communicate the patient-end connector with the suction connector. When the rotary switch is located in the second position, the communication between the patient-end connector and the suction connector is shut off.

11 Claims, 6 Drawing Sheets

SUCTION DEVICE HAVING A ROTARY SWITCH

BACKGROUND OF THE INVENTION

1. Field of the Invention

The present invention relates to a suction device, and in particular to a suction device having a rotary switch.

2. Description of Prior Art

Some patients lying on sickbeds cannot cough up their sputum by themselves. Thus, medical personnel has to use a suction device to suck the sputum of the patient. The conventional suction device includes a patient-end connector connected to the mouth and nose of the patient, an oxygen supply connector connected to an oxygen source, a suction connector, and a cleaning connector. In practice, oxygen coming from the oxygen source is delivered through the oxygen supply connector and the patient-end connector to enter the mouth and nose of the patient, thereby supplying oxygen to the patient continuously. In order to suck the sputum of the patient, the medical personnel has to insert a suction tube through the suction connector and into the patient-end connector, so that the sputum in the mouth and nose of the patient can be sucked into the suction tube by means of a negative pressure. After sucking the sputum of the patient completely, the medical personnel inserts a cleaning tube into the cleaning connector, so that a cleaning liquid is filled from the cleaning tube into the cleaning connector to thereby clean the remaining sputum in the suction device.

However, the conventional suction device is not provided with a switch, so that a portion of oxygen will be drawn out by the negative pressure of the suction tube. As a result, not all the oxygen is supplied to the patient during the sputum suction, and thus the patient feels uncomfortable because he/she does not breathe sufficient amount of oxygen. On the other hand, during a cleaning process of the suction tube, a portion of oxygen will be carried away by the cleaning liquid, and thus the patient also feels uncomfortable because he/she cannot breathe sufficient amount of oxygen. According to the above description, it is apparent that some oxygen is wasted.

The conventional suction device has another problem. After sucking the sputum completely, the medical personnel draws the suction tube out of the suction device and some sputum is adhered on the outer surface of the suction tube. The remaining sputum on the outer surface of the suction tube may infect the medical or cleaning personnel.

Therefore, the present Inventor aims to solve the above-mentioned problems.

SUMMARY OF THE INVENTION

The present invention is to provide a suction device having a rotary switch, which prevents the oxygen from being drawn out during the sputum suction and makes sputum unable to be remained on the outer surface of the suction tube.

The present invention is to provide a suction device having a rotary switch, including:

a main body, one end of the main body being provided with a patient-end connector and an oxygen supply connector in communication with the patient-end connector, the other end of the main body being provided with a suction connector and a cleaning connector in communication with the cleaning connector, the main body further having a connecting portion in communication with the cleaning connector; and a rotary switch, assembled with the connecting portion and switched between a first position and a second position, the rotary switch being provided with a cleaning liquid inlet in communication with the cleaning connector, a cleaning liquid outlet in communication with the cleaning liquid inlet and the suction connector, and two suction holes oppositely provided on both sides of the cleaning liquid inlet, the periphery of one of the suction holes adjacent to the suction connector being provided with a sputum-wiping piece;

whereby, the two suction holes are aligned with the patient-end connector and the suction connector when the rotary switch is located in the first position to thereby communicate the patient-end connector with the suction connector, the communication between the patient-end connector and the suction connector is shut off when the rotary switch is located in the second position.

According to another feature of the present invention, when the rotary switch is located in the first position, the periphery of one of the suction holes adjacent to the suction connector is provided with a sputum-wiping piece.

In comparison with prior art, the present invention has the following advantageous features:

According to the present invention, the suction device has a rotary switch provided with two opposite suction holes. The two suction holes are aligned with the patient-end connector and the suction connector when the rotary switch is located in the first position to thereby communicate the patient-end connector with the suction connector. At this time, the suction tube passing through the suction connector can enter the patient-end connector via these two suction holes, thereby sucking the sputum of the patient. Since the two suction holes are sized to merely allow the insertion of the suction tube, the oxygen provided from the oxygen supply connector cannot be drawn into the suction connector via the two suction holes. When the rotary switch is located in the second position, the two suction holes are not aligned with the patient-end connector and the suction connector and thus the communication between the patient-end connector and the suction connector is shut off. At this time, the cleaning liquid coming from the cleaning connector can flow through the cleaning liquid inlet and the cleaning liquid outlet to enter the suction connector, while the oxygen is blocked by the outer wall of the rotary switch from entering the suction connector. Therefore, the rotary switch of the present invention can prevent the oxygen from being drawn out during the sputum suction.

On the other hand, according to the present invention, when the rotary switch is located in the first position, the periphery of one of the suction holes adjacent to the suction connector is provided with a sputum-wiping piece. When the suction tube is drawn out of the two suction holes and the suction connector, the remaining sputum adhered onto the outer surface of the suction tube will be wiped away by the sputum-wiping piece to thereby stay in the rotary switch. In this way, sputum will not remain on the outer surface of the suction tube, so that medical and cleaning personnel can be prevented from being infected by the bacteria or virus in the sputum on the suction tube.

DETAILED DESCRIPTION OF THE INVENTION

The detailed description and technical contents of the present invention will become apparent with the following detailed description accompanied with related drawings. It is noteworthy to point out that the drawings is provided for the illustration purpose only, but not intended for limiting the scope of the present invention.

Figure 1:
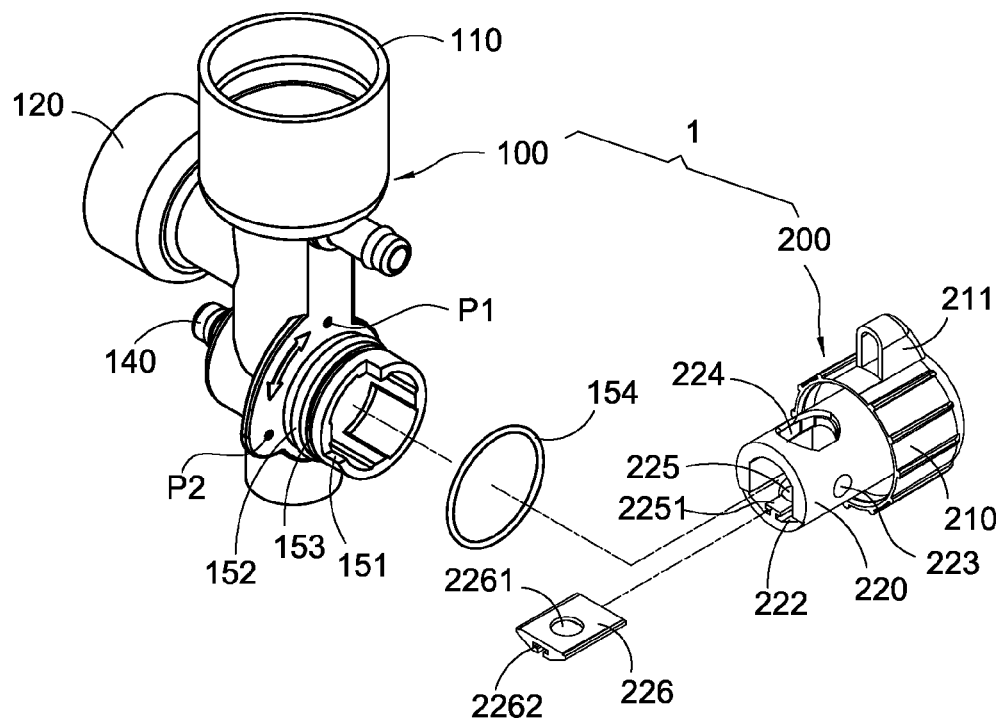
FIG. 1 is an exploded perspective view of the present invention.
Figure 2:
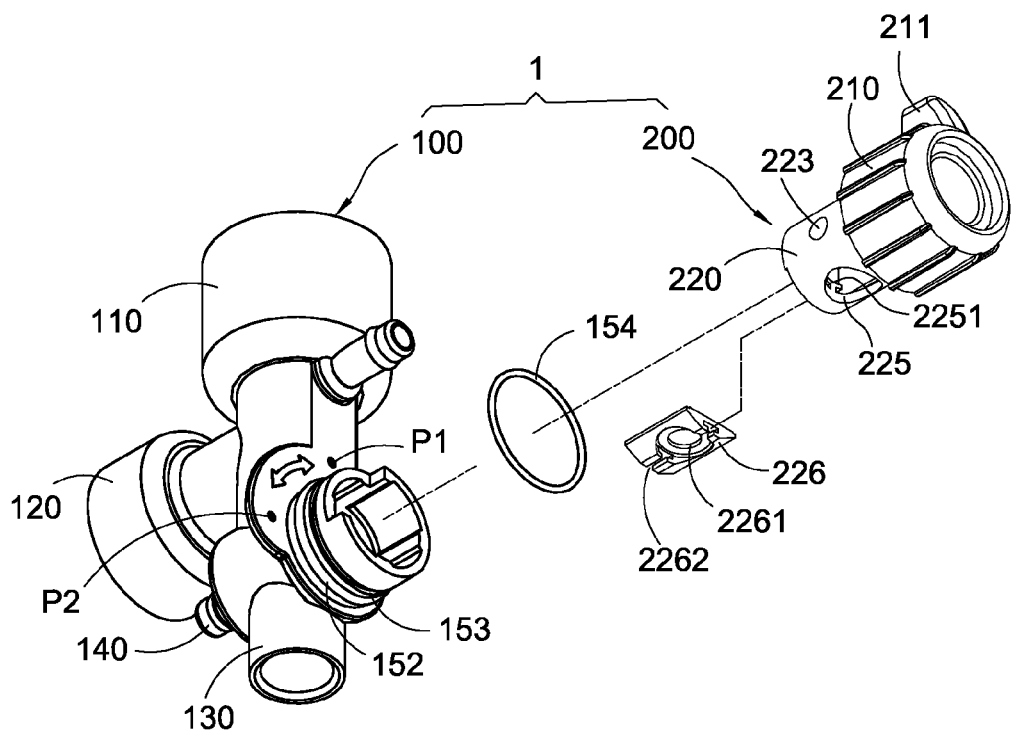
FIG. 2 is an exploded perspective view of the present invention taken from another viewing angle.
Figure 5:
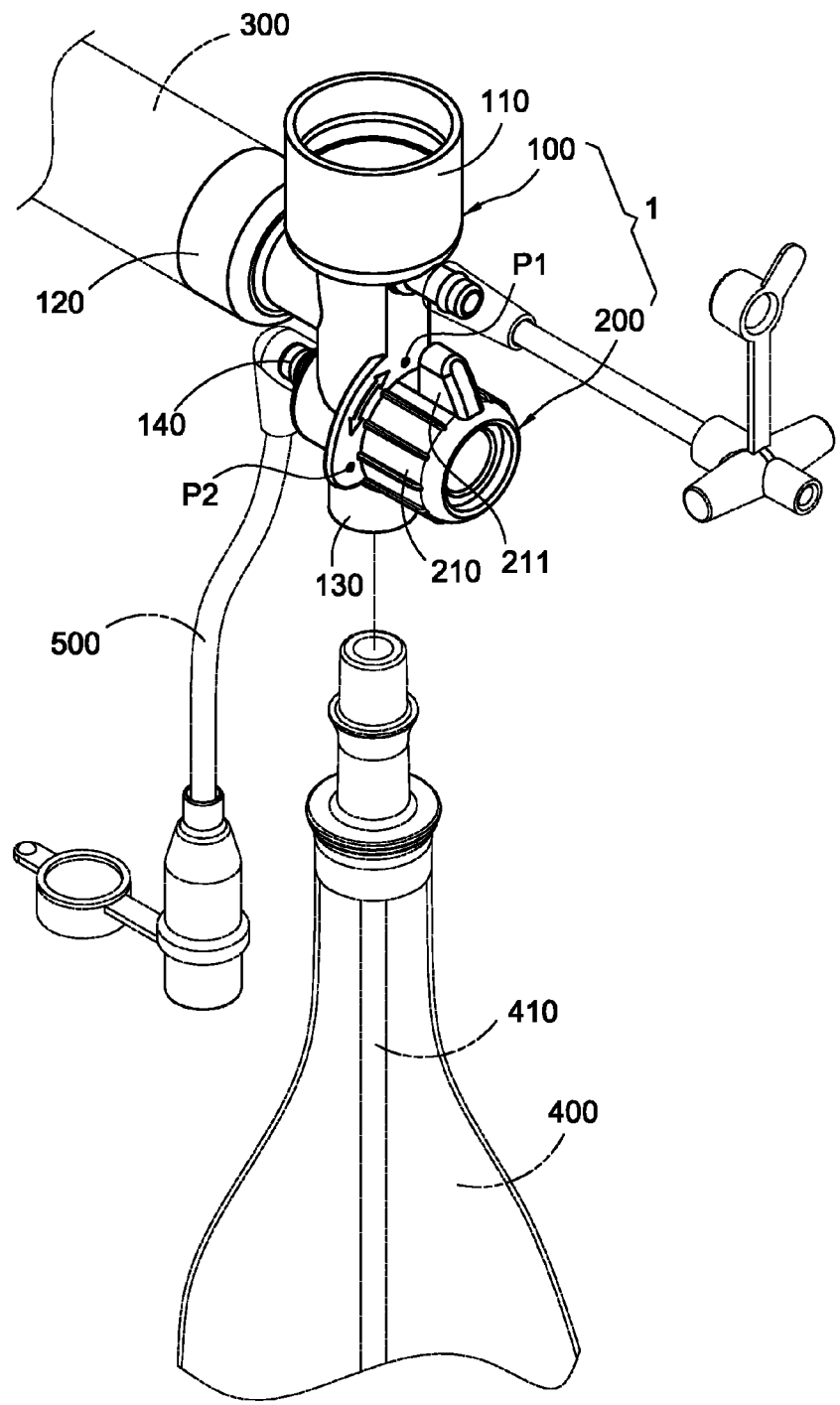
FIG. 5 is an exploded perspective view showing the rotary switch of the present invention in the first position and a suction tube.

Please refer to FIGS. 1, 2, and 5. The present invention provides a rotary switch 200 of a suction device. The suction device 1 has a main body 100. One end (upper end in FIG. 1) of the main body 100 is provided with a patient-end connector 110 connected to a mouth-nose mask M (FIG. 6) of a patient. Near the patient-end connector 110, the main body 100 is provided with an oxygen supply connector 120 in communication with the patient-end connector 110 and connected to an oxygen conduit 300. The other end (lower end in FIG. 1) of the main body 100 is provided with a suction connector 130 connected to a suction tube 410 of a sputum container 400. Near the suction connector 130, the main body is further provided with a cleaning connector 140 in communication with the suction connector 130 and connected to a cleaning tube 500.

The main body 100 of the suction device 1 further has a connecting portion 150 in communication with the cleaning connector 140. The connecting portion 150 is configured as a hollow tubular portion, so that the suction connector 130, the cleaning connector 140 and the connecting portion 150 form a T-joint structure. The connecting portion 150 is inserted by the rotary switch 200. The periphery of the connecting portion 150 is formed with a notch 151 occupying one quarter of the circumference of the connecting portion 150 (i.e. about 90 degrees) for restricting the rotation range of the rotary switch 200. The outer surface of the connecting portion 150 is formed with a flange 152. An annular groove 153 is provided between the flange 152 and the notch 151 for allowing a sealing ring 154 (such as an O-ring) to be disposed therein. The rotary switch 200 is assembled with the connecting portion 150 and such an assembly is shown in FIG. 6.

The rotary switch 200 is assembled with the connecting portion 150 and can be switched between a first position P1 and a second position P2. More specifically, the rotary switch 200 includes a rotary cover 210 and an insertion portion 220 protruding from the rotary cover 210 to be inserted into the connecting portion 150. The outer surface of the rotary cover 210 is formed with an indicating piece 211 for indicating the current position of the rotary switch 200.

Figure 3:
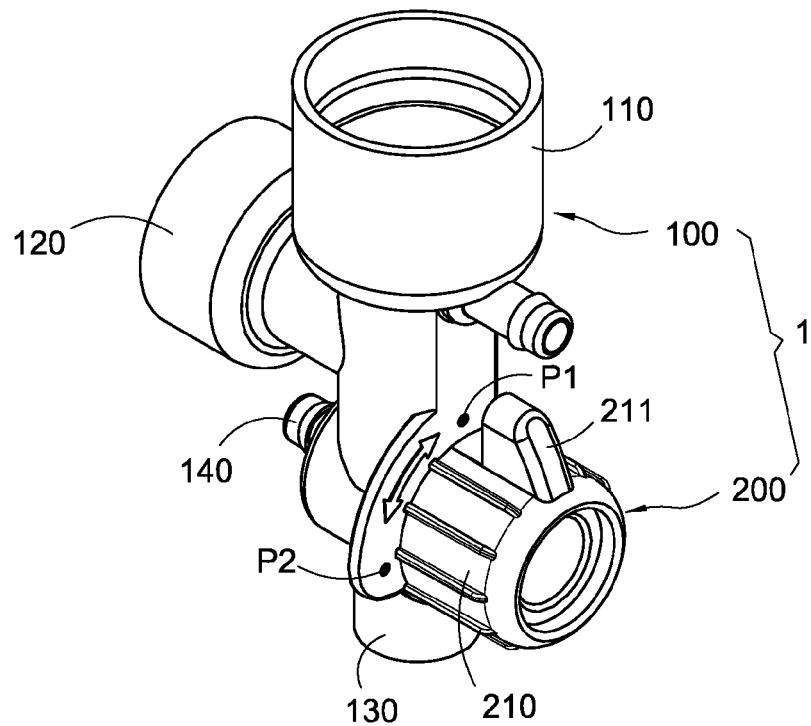
FIG. 3 is an assembled perspective view showing that the rotary switch of the present invention is located in the first position.
Figure 4:
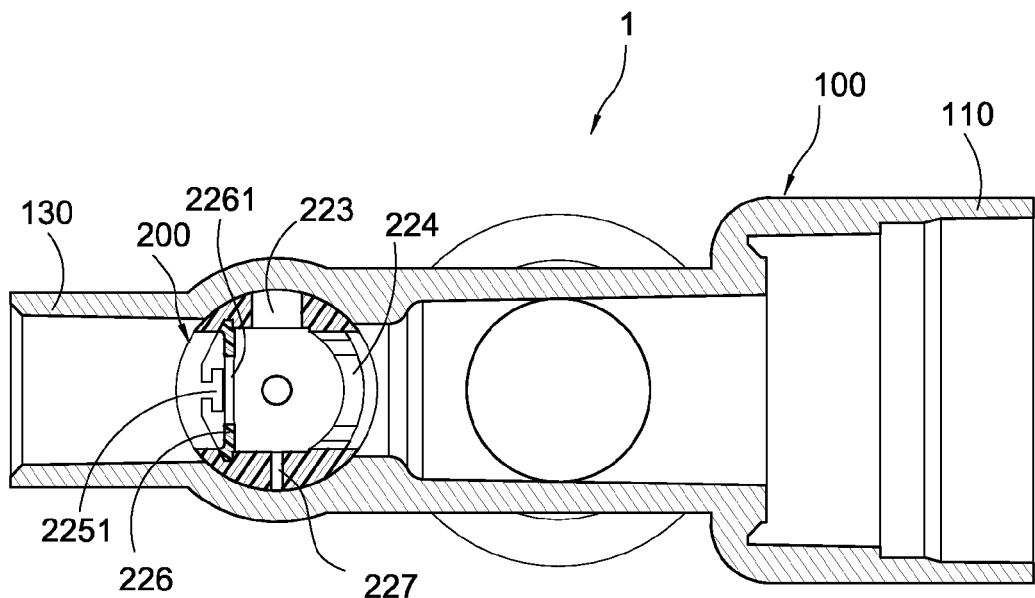
FIG. 4 is a cross-sectional view of FIG. 3.
Figure 6:
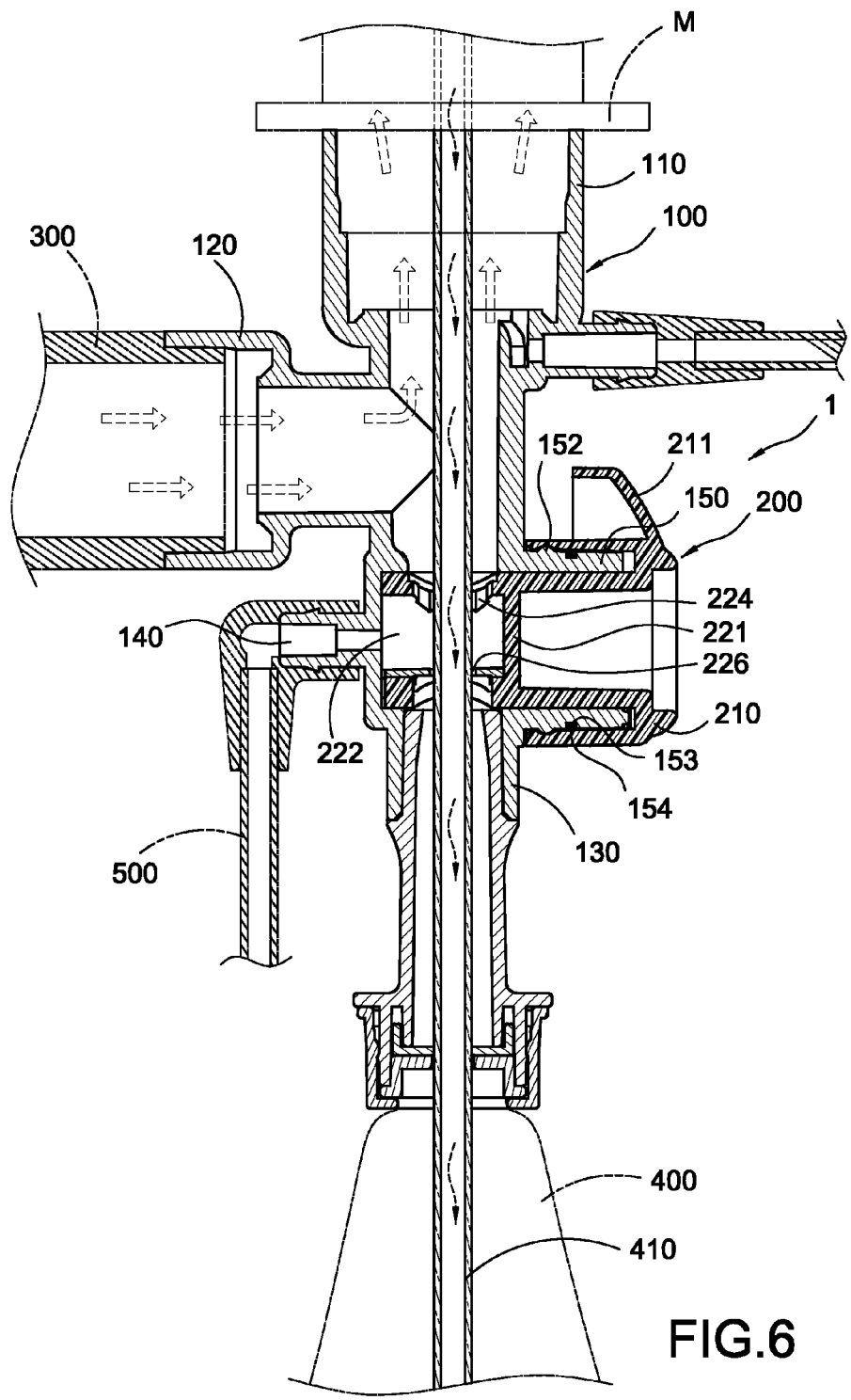
FIG. 6 is an assembled cross-sectional view showing the rotary switch of the present invention in the first position and the suction tube.

It can be seen from FIG. 6 that, the insertion portion 220 is configured as a tubular portion. The interior of the insertion portion 220 is formed with a partitioning plate 221 for separating the interior of the insertion portion 220 into two zones. A section of the insertion portion 220 adjacent to the cleaning connector 140 is formed with a cleaning liquid inlet 222 in communication with the cleaning connector 140. Further the outer wall of the insertion portion 220 is provided with a cleaning liquid outlet 112 in communication with the cleaning liquid inlet 222 and the suction connector 130, and two suction holes 224, 225 oppositely provided on both sides of the cleaning liquid inlet 222. More specifically, as shown in FIG. 1, the suction hole 224 is located in the same line as the indicating piece 211. Thus, when the rotary switch 200 is located in the first position P1 as shown in FIG. 3, that is, the indicating piece 211 is located in an upward-facing position, the two suction holes 224 and 225 are aligned with the patient-end connector 110 and the suction connector 130 in the vertical direction, thereby communicating the patient-end connector 110 with the suction connector 130 as shown in FIG. 4. The inner diameter of the suction hole 224, 225 is substantially equal to the outer diameter of the suction tube 410, so that the suction tube 410 can pass through the two suction holes 224, 225 in a tight-fit manner.

It should be noted that, as shown in FIG. 1, the periphery of one suction hole 225 of the two suction holes 224, 225 adjacent to the suction connector 130 is provided with a sputum-wiping piece 226. The sputum-wiping piece 226 has a through-hole 2261 whose inner diameter is slightly smaller than the outer diameter of the suction tube 410. Since the sputum-wiping piece 226 is made of flexible materials, the through-hole 2261 can be elastically deformed to allow the suction tube 410 to pass through and thus a tight fit is generated between the suction tube 410 and the sputum-wiping piece 226. When the suction tube 410 is removed from the suction holes 224 and 225, the remaining sputum adhered onto the outer surface of the suction tube 410 can be wiped away by the sputum-wiping piece 226.

In order to exchange the sputum-wiping piece 226, in the present embodiment of FIG. 1, the sputum-wiping piece 226 is not fixedly adhered to the suction hole 225. Instead, both sides of the suction hole 225 adjacent to the suction connector 130 are formed with an engaging protrusion 2251 respectively. One surface of the sputum-wiping piece 226 is provided with two troughs 2262 for allowing the two engaging protrusions 2251 to be engaged therein. By means of the engagement between the two troughs 2262 of the sputum-wiping piece 226 and the engaging protrusions 2251 of the suction hole 225, the sputum-wiping piece 226 can be detachably mounted to the suction hole 225.

As shown in FIG. 4, the wall of the connecting portion 220 is optionally provided with a ventilation hole 227 facing the cleaning liquid outlet 223. The diameter of the ventilation hole 227 is so small that it only allows little air to pass through to thereby facilitate the cleaning process of the suction tube 410. Of course, the ventilation hole 227 is optional. The cleaning process of the suction tube 410 can be still performed even without the ventilation hole 227 as long as the pressure of the cleaning liquid is large enough to push the liquid in the rotary switch 200.

Please refer to FIGS. 5 and 6. When the rotary switch 200 is located in the first position P1, the suction tube 410 of the sputum container 400 is inserted through the suction connector 130 and the two suction holes 224, 225 of the rotary switch 200 to enter the patient-end connector 110. As shown in the dotted arrows of FIG. 6, the oxygen coming from the oxygen conduit 300 flows through the oxygen supply connector 120 into the patient-end connector 110 without being affected by the suction tube 410. Furthermore, since the inner diameter of the suction hole 224, 225 is substantially equal to the outer diameter of the suction tube 410, the suction tube 410 passes through the suction holes 224, 225 in a tight-fit manner. Thus, the oxygen cannot flow into the suction connector 130 via the suction holes 224, 225. Therefore, during the sputum suction, the rotary switch 200 can prevent the oxygen from being drawn into the suction connector 130 and the sputum container 400. In this way, the waste of oxygen is avoided, and thus the patient will not feel uncomfortable as if he/she breathes insufficient amount of oxygen.

Figure 7:
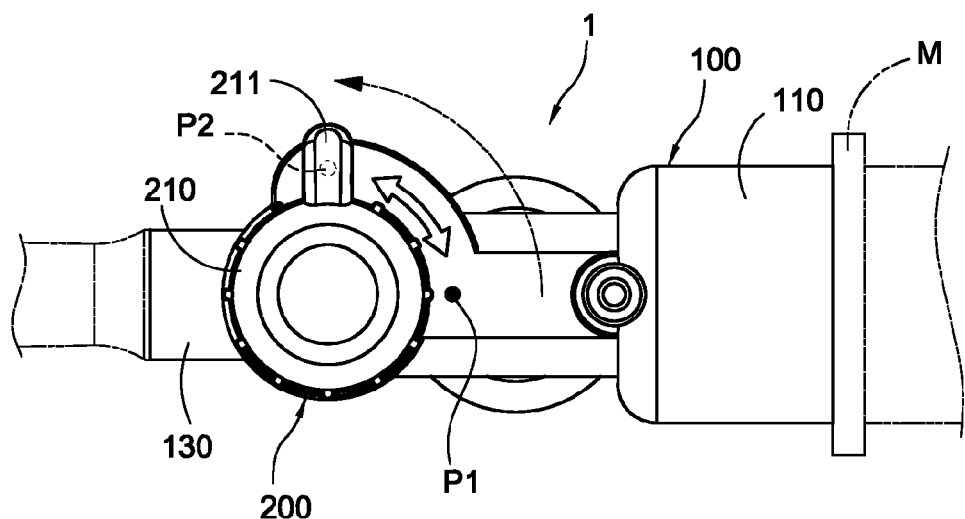
FIG. 7 is an assembled view showing the external appearance of the present invention when the rotary switch is located in the second position.
Figure 8:
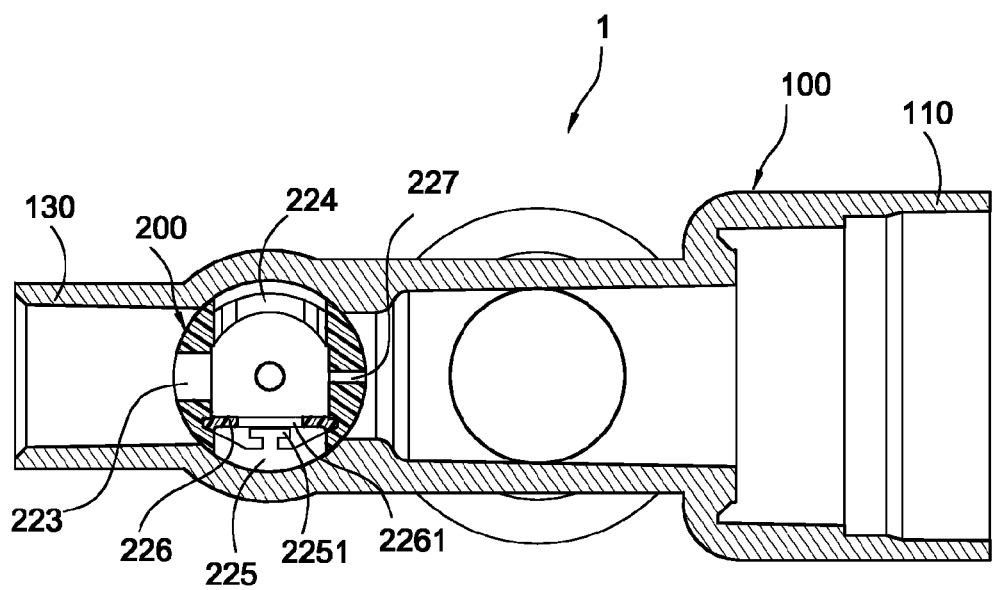
FIG. 8 is a cross-sectional view of FIG. 7.
Figure 9:
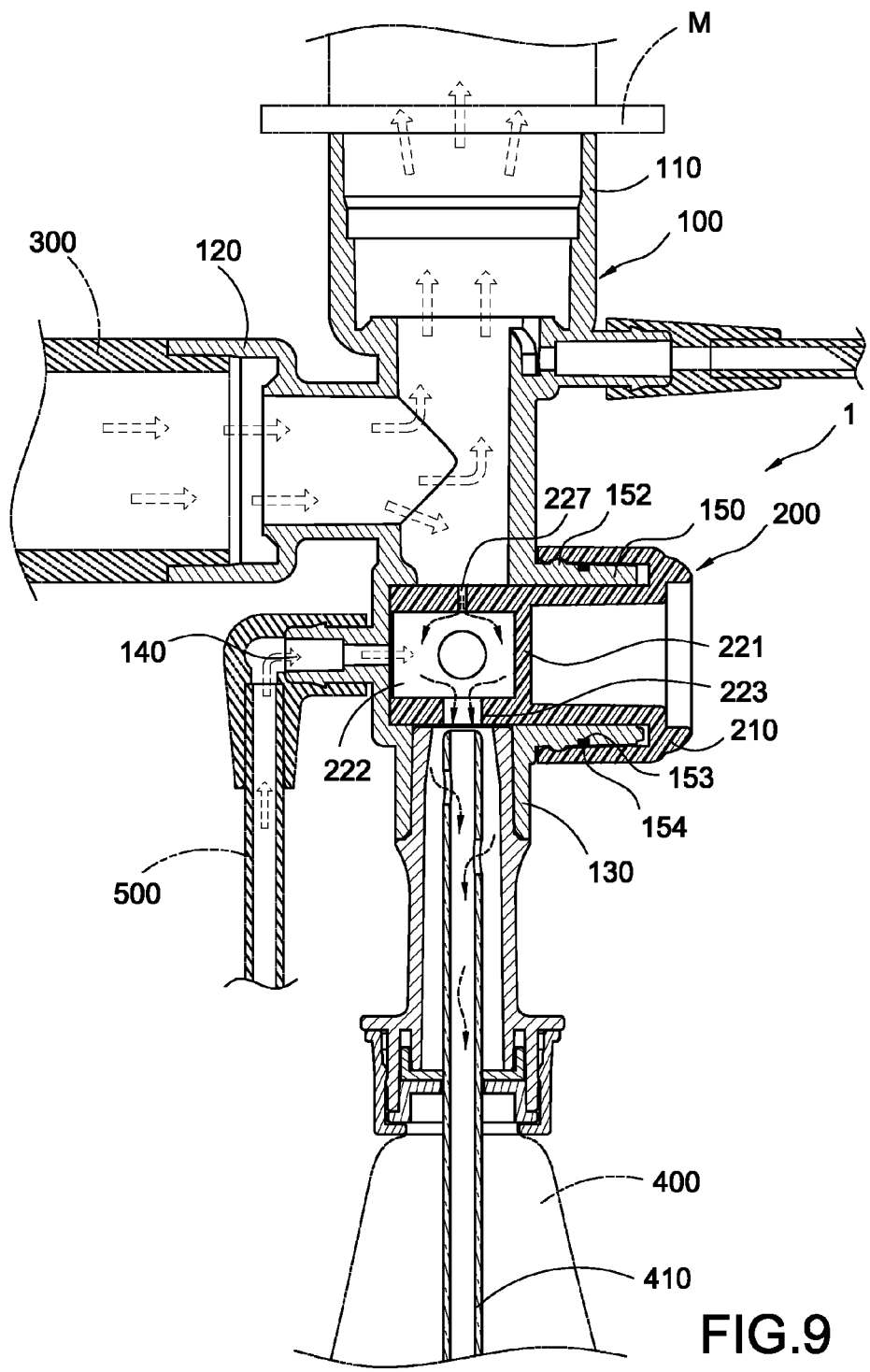
FIG. 9 is an assembled cross-sectional view showing the rotary switch of the present invention in the second position and the suction tube.

Please refer to FIGS. 7 to 9. When the rotary switch 200 is located in the second position P2, since the rotary switch 200 is rotated by approximate 90 degrees, the two suction holes 224, 225 are not any more aligned with the patient-end connector 110 and the suction connector 130, thereby shutting off the communication between the patient-end connector 110 and the suction connector 130. At this time, the cleaning liquid outlet 223 is in communication with the suction connector 130, while the ventilation hole 227 faces the patient-end connector 110. As shown in the larger dotted arrows of FIG. 9, the oxygen coming from the oxygen conduit 300 still smoothly flows into the oxygen supply connector 120 and the patient-end connector 110. Since the diameter of the ventilation hole 227 is small enough to block the oxygen from passing through. The cleaning liquid in the cleaning tube 500 flows from the cleaning connector 140 into the cleaning liquid inlet 222 of the insertion portion 220 of the rotary switch 200, and then flows into the suction tube 410 and the sputum container 400 via the cleaning liquid outlet 223.

In comparison with prior art, the present invention has the following advantageous features:

According to the present invention, the suction device 1 has a rotary switch 200 provided with two opposite suction holes 224 and 225. The two suction holes 224, 225 are aligned with the patient-end connector 110 and the suction connector 130 when the rotary switch 200 is located in the first position P1 to thereby communicate the patient-end connector 110 with the suction connector 130. At this time, the suction tube 410 passing through the suction connector 130 can enter the patient-end connector 110 via these two suction holes 224 and 225, thereby sucking the sputum of the patient. Since the two suction holes 224, 225 are sized to merely allow the insertion of the suction tube 410, the oxygen provided from the oxygen supply connector 120 cannot be drawn into the suction connector 130 via the two suction holes 224 and 225. When the rotary switch 200 is located in the second position P2, the two suction holes 224, 225 are not aligned with the patient-end connector 110 and the suction connector 130 and thus the communication between the patient-end connector 110 and the suction connector 130 is shut off. At this time, the cleaning liquid coming from the exterior into the cleaning connector 120 will flow through the cleaning liquid inlet 222 and the cleaning liquid outlet 223 into the suction connector 130, while the oxygen is blocked by the outer wall of the rotary switch 200 from entering the suction connector 130. Therefore, the rotary switch 200 of the present invention can prevent the oxygen from being drawn out during the sputum suction.

On the other hand, according to the present invention, when the rotary switch 200 is located in the first position P1, the periphery of the suction hole 225 adjacent to the suction connector 130 is provided with a sputum-wiping piece 226. When the suction tube 410 is drawn out of the two suction holes 224, 225 and the suction connector 130, the remaining sputum adhered onto the outer surface of the suction tube 410 will be wiped away by the sputum-wiping piece 226 to thereby stay in the rotary switch 200. In this way, sputum will not remain on the outer surface of the suction tube 410, so that the medical and cleaning personnel can be prevented from being infected by the bacteria or virus in the sputum adhered on the suction tube 410.

Although the present invention has been described with reference to the foregoing preferred embodiments, it will be understood that the invention is not limited to the details thereof. Various equivalent variations and modifications can still occur to those skilled in this art in view of the teachings of the present invention. Thus, all such variations and equivalent modifications are also embraced within the scope of the invention as defined in the appended claims.

What is claimed is:

1. A suction device having a rotary switch, including:
   a main body (100), one end of the main body (100) being provided with a patient-end connector (110) and an oxygen supply connector (120) in communication with the patient-end connector (110), the other end of the main body (100) being provided with a suction connector (130) and a cleaning connector (140) in communication with the suction connector (130), the main body (100) further having a connecting portion (150) in communication with the cleaning connector (140); and
   a rotary switch (200), assembled with the connecting portion (150) and switched between a first position (P1) and a second position (P2), the rotary switch (200) being provided with a cleaning liquid inlet (222) in communication with and facing to the cleaning connector (140), a cleaning liquid outlet (223) in communication with the cleaning liquid inlet (222) and facing to the suction connector (130) when the rotary switch (200) located at the second position (P2), and two suction holes (224, 225) oppositely provided on both sides of the cleaning liquid inlet (222), the periphery of the suction hole (225) adjacent to the suction connector (130) being provided with a sputum-wiping piece (226) which is located inside the rotary switch (200);
   whereby, the two suction holes (224, 225) are aligned with the patient-end connector (110) and the suction connector (130) when the rotary switch (200) is located at the first position (P1) to thereby communicate the patient-end connector (110) with the suction connector (130), and the communication between the patient-end connector (110) and the suction connector (130) is shut off when the rotary switch (200) is located at the second position (P2).

2. The suction device having a rotary switch according to claim 1, wherein the connecting portion (150) is configured as a hollow tubular portion, so that the suction connector (130), the cleaning connector (140) and the connecting portion (150) form a T-joint structure.

3. The suction device having a rotary switch according to claim 1, wherein the periphery of the connecting portion (150) is formed with a notch (151) for restricting the rotation range of the rotary switch (200).

4. The suction device having a rotary switch according to claim 3, wherein an outer surface of the connecting portion (150) is formed with a flange (152), an annular groove (153) is provided between the flange (152) and the notch (151) for allowing a sealing ring (154) to be disposed therein.

5. The suction device having a rotary switch according to claim 1, wherein the rotary switch (200) includes a rotary cover (210) and an insertion portion (220) protruding from the rotary cover (210) to be inserted into the connecting portion (150).

6. The suction device having a rotary switch according to claim 5, wherein a wall of the insertion portion (220) is optionally provided with a ventilation hole (227) facing the cleaning liquid outlet (223).

7. The suction device having a rotary switch according to claim 5, wherein the rotary cover (210) is provided with an indicating piece (211) for indicating the current position of the rotary switch (200).

8. The suction device having a rotary switch according to claim 7, wherein the suction hole (224) adjacent to the patient-end connector (110) is located in the same line as the indicating piece (211) when the rotary switch (200) is located in the first position (P1), the other suction hole (225) is located adjacent to the suction connector (130).

9. The suction device having a rotary switch according to claim 7, wherein the inner diameter of the two suction holes (224, 225) is equal to the outer diameter of the suction tube (410), so that the suction tube (410) can pass through the two suction holes (224, 225) in a tight-fit manner when the rotary switch (200) located at the first position (P1).

10. The suction device having a rotary switch according to claim 9, wherein the sputum-wiping piece (226) has a through-hole (2261) for allowing the suction tube (410) to pass through.

11. The suction device having a rotary switch according to claim 10, wherein both sides of the suction hole (225) adjacent to the suction connector (130) are formed with an engaging protrusion (2251) respectively, one surface of the sputum-wiping piece (226) is provided with two troughs (2262) for allowing the two engaging protrusions (2251) to be engaged therein.

\* \* \* \* \*